(12) United States Patent
O'Neill

(10) Patent No.: US 11,759,484 B2
(45) Date of Patent: Sep. 19, 2023

(54) COMPOSITIONS AND USES THEREOF

(71) Applicant: SkinBioTherapeutics PLC, Macclesfield (GB)

(72) Inventor: Catherine O'Neill, Macclesfield (GB)

(73) Assignee: SkinBioTherapeutics PLC, Macclesfield (GB)

( * ) Notice: Subject to any disclaimer, the term of this patent is extended or adjusted under 35 U.S.C. 154(b) by 0 days.

(21) Appl. No.: 17/053,446

(22) PCT Filed: May 9, 2019

(86) PCT No.: PCT/GB2019/051270
§ 371 (c)(1),
(2) Date: Nov. 6, 2020

(87) PCT Pub. No.: WO2019/215446
PCT Pub. Date: Nov. 14, 2019

(65) Prior Publication Data
US 2021/0244779 A1  Aug. 12, 2021

(30) Foreign Application Priority Data
May 9, 2018 (GB) ..................................... 1807576

(51) Int. Cl.
*A61K 39/00* (2006.01)
*A61K 35/747* (2015.01)
*A61K 8/99* (2017.01)

(52) U.S. Cl.
CPC .............. *A61K 35/747* (2013.01); *A61K 8/99* (2013.01)

(58) Field of Classification Search
CPC .................................................... A61K 35/747
See application file for complete search history.

(56) References Cited

U.S. PATENT DOCUMENTS
2015/0079040 A1   3/2015   O'Neill et al.

FOREIGN PATENT DOCUMENTS

| RU | 2014145534 | 3/2013 |
| WO | WO 2011/029784 | 3/2011 |
| WO | WO 2015/181534 | 12/2015 |
| WO | WO 2017/015275 | 1/2017 |
| WO | WO 2017/164681 | 9/2017 |
| WO | WO 2017/199022 | 11/2017 |

OTHER PUBLICATIONS

ATCC (American Tissue Culture Collection), "Lactobacillus rhamnosus: Accession No. ATCC 53103," Product Sheet, Sep. 2019.
Hankook Cosmetics Mfg. Co. Ltd., Database WPI, Week 201806, Thomson Scientific, London: GB, XP002793073, Dec. 2017.
Marsella et al., "Investigation of the effect of probiotic exposure on filaggrin expression in an experimental model of canine atopic dermatitis," Veterinary Dermatology, vol. 24(2):261-263, Feb. 2013.
Mohammedsaeed et. al., "Lactobacillus rhamnosus GG Inhibits the Toxic Effects of *Staphylococcus aureus* on Epidermal Keratinocytes," Appl. Environ. Microbiol., vol. 80(18):5773-5781, Sep. 2014.
Prince et. al., "Lactobacillus reuteri Protects Epidermal Keratinocytes from *Staphylococcus aureus*-Induced Cell Death by Competitive Exclusion," Appl Environ. Microbiol., vol. 78(15):5119-26, Aug. 2012 (Epub May 2012).
Wu et al., "Evaluation of efficacy and safety of Lactobacillus rhamnosus in children aged 4-48 months with atopic dermatitis: An 8-week, double-blind, randomized, placebo-controlled study," Journal of Microbiology, Immunology and Infection, vol. 50(5):684-692, Nov. 2015.
International Search Report and Written Opinion issued on International Patent Application No. PCT/GB2019/051270, dated Jul. 30, 2019.
Search Report issued on UK Patent Application No. GB 1807576.2, dated Nov. 22, 2018.

*Primary Examiner* — Albert M Navarro
(74) *Attorney, Agent, or Firm* — Howson & Howson LLP; Colleen M. Schaller; Francis J. Coffey

(57) ABSTRACT

The present invention relates to a composition comprising *Lactobacillus rhamnosus* GG (LGG) (ATCC 53103) and/or a bioactive extract of LGG to increase the expression of filaggrin or profilaggrin, for use in treating skin or mucosa barrier dysfunctions or defects. The present invention also comprises the use of a composition comprising *Lactobacillus rhamnosus* GG (LGG) (ATCC 53103) and/or a bioactive extract of LGG to increase the expression of filaggrin or profilaggrin, for use in the manufacture of a medicament for use in treating skin barrier dysfunctions. Also disclosed is a use of a composition comprising *Lactobacillus rhamnosus* GG (LGG) (ATCC 53103) and/or a bioactive extract of LGG to increase the expression of filaggrin or profilaggrin, for use in the manufacture of a cosmetic composition for use in improving the appearance and/or texture of the skin. The present invention also comprises a method of treating skin barrier dysfunctions comprising administering a composition comprising *Lactobacillus rhamnosus* GG (LGG) and/or a bioactive extract of LGG to increase the expression of filaggrin or profilaggrin.

6 Claims, 2 Drawing Sheets

COMPOSITIONS AND USES THEREOF

CROSS-REFERENCE TO RELATED APPLICATIONS

This application is a National Stage Entry under 35 U.S.C. 371 of International Patent Application No. PCT/GB2019/051270, filed May 9, 2019, which claims priority to UK Patent Application No. GB 1807576.2, filed May 9, 2018. These applications are incorporated by reference herein.

FIELD OF THE INVENTION

The present invention relates to compositions comprising probiotic *Lactobacillus rhamnosus* GG (LGG) and/or bioactive extracts of LGG. The compositions are particularly suited for use in improving the skin barrier and mucosa and treating dermatological disorders or defects.

BACKGROUND TO THE INVENTION

Atopic Dermatitis (AD), also known as atopic eczema, is a chronic inflammatory skin condition. AD is the most common form of eczema and currently affects approximately 20% of the paediatric population in the western world. AD causes the skin to become itchy, red, dry and cracked. Scratching worsens symptoms and affected people have an increased risk of skin infections. If the skin barrier is breached irritants such as soaps and detergents can dry the skin and further deteriorate the weakened skin barrier. Food, microbes and other allergens can also penetrate the upper layers of the skin potentially causing allergic reactions. Some people may only have small patches of dry skin, but others may experience widespread red, inflamed skin all over the body.

Treatments used to control symptoms and manage AD include self care techniques, such as reducing scratching and avoiding triggers, emollients (moisturising treatments) and topical corticosteroids, including hydrocortisone, clobetasone butyrate and mometasone, used to reduce swelling, redness and itching during flare-ups.

Topical corticosteroids can cause a mild stinging sensation upon application and in rare cases can result in thinning of the skin, skin thickening, stretch marks, changes in skin colour, acne and increased hair growth. Less common but more severe side effects of steroids include glaucoma, cataracts, tiny pink bumps on the skin, red pus-filled hair follicles, adrenal suppression and topical steroid addiction/withdrawal. For particularly severe flare-ups corticosteroid tablets may be prescribed but courses of treatment longer than about 7 days are generally avoided because of the risk of potentially serious side effects.

Alternative non-steroidal AD treatments include topical calcineurin inhibitors that suppress the immune system such as pimecrolimus and tacrolimus, phototherapy, bandages or wet wraps, immunosuppressant tablets, and alitretinoin to treat severe eczema affecting the hands in adults. There have been concerns that calcineurin inhibitors may increase the risk of skin cancer or lymphoma.

Filaggrin (filament aggregating protein) is an important filament-associated, barrier protein expressed in the stratum corneum that binds to keratin fibres in epithelial cells. Filaggrin is vital for the formation of the outermost protective layer of skin known as the cornified cell envelope (CCE). In addition filaggrin helps to form part of the natural moisturising substance of the skin by its unfolding and degradation into hygroscopic amino acids. Low levels of filaggrin may lead to a leaky skin barrier which then allows entry of pathogenic bacteria such as *S. aureus* which induce the flares, characteristic of AD.

Although AD is not all one phenotype, a significant number of individuals presenting with the disease have polymorphisms in the gene for filaggrin (FLG). Individuals with mutations in FLG are strongly predisposed to a severe form of dry skin ichthyosis vulgaris and/or atopic eczema. It has been shown that almost 50% of all severe cases of eczema may have at least one mutated filaggrin gene.

Probiotics have been defined as 'live micro-organisms which, when administered in adequate amounts, confer a health benefit to the host'. Usually members of the genera lactobacilli and bifidobacteria, probiotics have been reported to have beneficial effects when consumed orally, such as prevention of antibiotic associated diarrhoea and prevention of atopic disease.

Since probiotics may have positive impacts on the gut, their potential effects on other systems, such as the mouth and the urogenital tract have also begun to be investigated. A study examining the impact of oral administration of Lactobacilli in a clinical trial of women with bacterial vaginosis, showed that Lactobacilli could indeed inhibit the colonization of uro-epithelial cells by pathogens. Recently, the topical application of probiotics to the skin has been investigated in a limited number of studies. Topical application of sonicated *Streptococcus salivarius* strains to patients suffering from atopic dermatitis resulted in improved barrier function apparently through increasing the level of ceramides in the stratum corneum. Topically applied *L. plantarum* for treatment of infected wounds resulted in improved tissue repair in a mouse burn model and prevention of infection in chronic leg ulcers and burns in humans. However, in general the mechanisms underlying these effects are not well understood.

WO2017/015275 has shown compositions and methods comprising a strain of *Lactobacillus fermentum* can be used for treating human dermatological conditions by employing a microbiome-centered treatment approach.

The inventors have previously shown that the probiotic bacterium *Lactobacillus rhamnosus* GG can inhibit *Staphylococcus aureus* infection of human primary keratinocytes in culture (see WO2015/181534). They have also shown that *L. rhamnosus* LGG can inhibit *S. aureus* adhesion to primary human keratinocytes protecting epidermal keratinocytes from the toxic effects of *S. aureus* (see WO2017/199022).

The recognition of the importance of filaggrin to skin barrier function has prompted investigation into enhancing its expression in healthy skin as a means of augmenting the barrier.

SUMMARY OF THE INVENTION

The invention is defined in the appended claims and also includes the combination of the aspects and preferred features hereinafter described except where such a combination is clearly impermissible or expressly avoided.

In accordance with a first aspect of the present invention, there is provided a composition comprising *Lactobacillus rhamnosus* GG (LGG) (ATCC 53103) and/or a bioactive extract of LGG, to increase the expression of filaggrin or profilaggrin, for use in the prevention, management, amelioration or treatment of skin or mucosa barrier dysfunctions or defects.

The invention relates to probiotic bacteria of the species *Lactobacillus rhamnosus*. Such bacteria were originally considered a subspecies of *Lactobacillus casei*, but later genetic research found it to be a species of its own. The invention relates to *L. rhamnosus* GG. *L. rhamnosus* GG (also referred to herein as LGG) is deposited at ATCC (American Tissue Culture Collection) under accession number ATCC 53103. LGG was isolated in 1983 from the intestinal tract of a healthy human being by Gorbach and Goldin.

The composition may comprise LGG and/or a bioactive extract of LGG in a lyophilised, freeze-dried or lysate form. Preferably the composition comprises LGG and/or a bioactive extract of LGG in lysate form. The lysate form may then be further processed or formulated so that it can be topically delivered to the skin or other external barriers (such as mucosa)

The composition may be for use in preventing a reduction in skin or mucosa barrier function, in repair of skin or mucosa barrier function, to regenerate skin or mucosa barrier function or to increase skin or mucosa barrier function. Most preferably the composition is for use in increasing and/or reparining skin or mucosa barrier function.

Preferably the composition is for use in increasing the expression of one or more skin or mucosa barrier proteins. Most preferably the composition is for use in increasing the expression of filaggrin or profilaggrin. Advantageously the inventors have demonstrated that applying LGG lysate to skin samples increased the expression of filaggrin and/or profilaggrin (or potentially other filaggrin precursors).

The composition may be for use in treating atopic dermatitis, ichthyosis vulgaris or atopic eczema. The use of a composition comprising *Lactobacillus rhamnosus* GG (LGG) and/or a bioactive extract of LGG advantageously avoids the side effects seen with corticosteroids which are frequently prescribed for the treatment of atopic dermatitis.

The composition may comprise an effective amount of LGG and/or a bioactive extract of LGG for use in treating skin or mucosa barrier dysfunctions or defects. The composition may comprise an effective amount of LGG and/or a bioactive extract of LGG for use in restoring or increasing Filaggrin or Profilaggrin levels to a skin or mucosa barrier. The composition may comprise 1 µg or more of LGG and/or a bioactive extract of LGG. Most preferably the composition comprises 2.5-7.5 µg of a lysate of LGG and/or a bioactive extract of LGG.

In accordance with a further aspect of the present invention, there is provided a composition comprising a *Lactobacillus* strain and/or a bioactive extract of a *Lactobacillus* strain for use in increasing the expression of filaggrin or profilaggrin (or other filaggrin precursor).

The *Lactobacillus* strain may comprise *Lactobacillus rhamnosus*. Preferably the *Lactobacillus rhamnosus* comprises *Lactobacillus rhamnosus* GG (LGG) (ATCC 53103).

The composition may be for use in the prevention, management, amelioration or treatment of skin or mucosa barrier dysfunctions or defects.

Alternatively, the composition may be for use cosmetically to improve skin barrier dysfunctions or defects.

The composition may be for cosmetic use. The composition may be for cosmetic use in improving the appearance and/or texture of the skin.

The composition may suitably be in the form of a liquid, solution (e.g., aqueous, non-aqueous), suspension (e.g., aqueous, non-aqueous), emulsion (e.g., oil-in-water, water-in-oil), elixir, syrup, electuary, mouthwash, cavity wash, drops, granules, powders, ampoule, bolus, suppository, pessary, tincture, gel, paste, ointment, cream, lotion, oil, foam, spray, mist, or aerosol.

The composition may suitably be provided as part of a patch, adhesive plaster, bandage, dressing, or the like which is impregnated with one or more active compounds and optionally one or more other pharmaceutically acceptable ingredients, including, for example, penetration, permeation, and absorption enhancers. The composition may also suitably be provided in the form of a depot or reservoir. The composition may also be provided in the form of coatings for medical devices such as implants, prosthetics, surgical instruments, gloves, catheters, valves, pacemakers and the like.

The compositions according to the aspects of the invention may further comprise one or more pharmaceutically or cosmetically acceptable ingredients or excipients. Pharmaceutically acceptable ingredients are well known to those skilled in the art, and include, but are not limited to, pharmaceutically acceptable carriers, adjuvants, excipients, diluents, fillers, buffers, preservatives, 3 carriers, excipients, diluents, fillers, buffers, preservatives, anti-oxidants, lubricants, stabilisers, solubilisers, surfactants (e.g. wetting agents), masking agents, colouring agents, fragrance agents and penetration agents.

The compositions according to the aspects of the invention may further comprise a carrier. The carrier is usually a solution in which the *Lactobacillus rhamnosus* GG (LGG) and/or bioactive extract of LGG is dissolved, suspended, diluted or admixed.

In some cases the carrier may comprise the medium which has been in contact with the bacterium during culturing. The composition of the medium will have changed during the culture, for example by the secretion of material from the bacterium. The compositions may consist or comprise culture medium in which the bacteria have been grown.

In embodiments the composition according to the invention is formulated for intranasal, pulmonary, buccal, oral or topical administration. Preferably the composition is formulated for topical administration particularly for use or application to, or on, the skin. The composition may be formulated for topical administration in the form of gels, pastes, ointments, creams, lotions, and oils, as well as patches, adhesive plasters, bandages, dressings, depots, cements, glues, and reservoirs. Preferably the composition may be formulated for topical administration in the form of a cream, gel, ointment or oil.

Ointments are typically prepared from the composition and a paraffinic or a water-miscible ointment base.

Creams are typically prepared from the extract and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the LGG and/or a bioactive extract of LGG and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulsion and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

The composition may be administered alone or in combination with other treatments, either simultaneously or sequentially. Compositions according to the invention may further comprise other active agents, for example antibacterial agents such as bactericidal agents.

In some embodiments, the composition may be provided as a suspension in a pharmaceutically or cosmetically acceptable excipient, diluent or carrier.

The compositions of the present invention may be formulated as medicaments, that is to say formulated as a medicine, or a medical device. The medicament may include other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g. wetting agents), masking agents, colouring agents, flavouring agents, and sweetening agents. The formulation may further comprise other active agents, for example other therapeutic or prophylactic agents.

Media suitable for culturing bacteria (such as *L. rhamnosus*) is well known to those of skill in the art. As used herein the terms "media" and "medium" encompasses any nutrient containing liquid in which bacteria may be supported, kept alive, grown and/or expanded. The media may contain the minimal nutrients to support bacterial life, and optionally other nutrients. Exemplary nutrients contained within the broth include sugar, magnesium, phosphate, phosphorous and sulphur. The media may be made to, or modified from, a combination of nutrients that is well known in the art, such as Wilkins-Chalgren Broth. Media may be obtained pre-mixed from a commercial source, or may be made in-house.

Preferably the composition is cell free and does not contain any live bacterial cells. The whole bacterial cells may have been removed from the media, for example by centrifugation and/or filtration (or other suitable method for removing live bacteria). For example, the bacteria may be removed by sedimenting them from the media in a centrifuge at 15,000×g for a period of time sufficient for substantially all of the bacteria to sediment from the media. The media may be filtered using a microporous filter with pores of a suitable size to remove substantially all of the bacteria from the media. These methods may remove intact bacteria, and may also remove bacterial debris, if the extract is derived by cell lysis.

The composition may be sterile. That is to say that the composition has been subject to a sterilisation process, such as irradiation, heat, chemicals, pressure or filtration, or any combination thereof. However, such sterilisation procedures must be adapted so as not to damage or reduce the efficacy of LGG and/or bioactive extract. In the case of media containing an extract, the media may have been sterilised before LGG were introduced and cultured, and also after the bacteria had been removed from that media.

In some cases the extract of the composition contains substantially no intact bacteria. The composition may also be substantially free from lysed bacteria or bacterial fragments. The intact bacteria and/or lysed bacteria or bacterial fragments may have been separated from the extract. Separation may occur by any suitable means known in the art, such as centrifugation or filtration. By "substantially free from" we mean that the extract contains no or minimal contamination of non-secreted bacterial components, such as whole bacteria, lysed bacteria, or bacterial fragments. Thus, the composition may contain 100% extract, at least 99% extract, at least 95% extract, at least 90% extract, at least 85% extract, at least 80% extract, at least 75% extract or at least 70% extract. The extract may comprise additional components of non-bacterial origin, such as carrier solutions, other active agents, or preservatives, as described herein.

Compositions as described herein may be prepared by culturing LGG in media, separating LGG from the media, and preparing a composition from the media. The LGG bacteria may be cultured under anaerobic conditions. The LGG bacteria may be cultured at a temperature above the normal temperature of the human body. The LGG bacteria may be cultured at 30° C., 31° C., 32° C., 33° C., 34° C., 35° C., 36° C., 37° C., 38° C., 39° C., 40° C. or 41° C. Preferably the bacteria are cultured at 37° C. The bacteria may be cultured in the media for 1 day, 2 days, 3 days, 4 days, 5 days, 6 days, 7 days, 8 days, 9 days, 10 days, 11 days, 12 days, 13 days or 14 days. The LGG bacteria or lysed LGG bacteria or fragments of LGG bacteria may be separated from the media by centrifugation, such as centrifugation at 15000×g. The media may be separated from the LGG bacteria, lysed LGG bacteria or fragments of LGG bacteria by filtration. The media may be separated by a combination of filtration and centrifugation. The media may be subject to sterilisation, before or after the LGG bacteria are removed. For example, following separation of the media from the whole bacteria, lysed bacteria or bacterial fragments, the media may be subject to sterilisation. The media may be subject to concentration, such that the proportion of LGG extract increases relative to the total volume of media. Concentration may occur by any method known in the art, such as evaporation. The LGG extract may be separated from the media. Any method of separating material from a carrier solution may be used. For example the LGG extract may be separated from the media by chromatography, crystallisation, distillation, drying, electrophoresis or precipitation. Once isolated from the media, or concentrated in the media, the extract may be dissolved or diluted in a carrier, or otherwise formulated into a composition as disclosed herein.

In additional aspects of the invention there is also provided a use of a composition comprising *Lactobacillus rhamnosus* GG (LGG) (ATCC 53103) and/or a bioactive extract of LGG for use in the manufacture of a medicament for use in treating skin barrier dysfunctions, wherein the composition increases the expression of filaggrin or profilaggrin.

In a further aspect of the invention there is provided a use of a composition comprising *Lactobacillus rhamnosus* GG (LGG) (ATCC 53103) and/or a bioactive extract of LGG for use in the manufacture of a cosmetic composition for use in improving the appearance and/or texture of the skin, wherein the composition increases the expression of filaggrin or profilaggrin.

In an additional aspect of the invention there is provided a method of treating skin or mucosa barrier dysfunctions or defects comprising administering a composition comprising *Lactobacillus rhamnosus* GG (LGG) (ATCC 53103) and/or a bioactive extract of LGG, wherein the composition increases the expression of filaggrin or profilaggrin.

The preferred and alternative features described above in relation to the first aspect of the invention also apply to the additional and further aspects of the invention.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which.

EXAMPLES

Example 1

Bacterial Cell Culture

*Lactobacillus rhamnosus* GG (ATCC 53103) was cultured anaerobically in Wilkins-Chalgren broth at 37° C., and *Staphylococcus aureus* was cultured aerobically in nutrient broth (Oxoid) as described in Mohammedsaeed et. al. (2014) and Prince et. al. (2011) (Mohammedsaeed M., et. al., (2014). *Appl. Environ. Microbiol.* 80(18):5773 and Prince T. et. al., (2011) *Appl Environ. Microbiol.* 78(15):5119-26). LGG lysate was produced according to the protocol published in Mohammedsaeed et. al., (2014).

Preparation of Skin

Healthy human skin was obtained from elective plastic surgery procedures. 6 mm biopsies of said skin were prepared and maintained in organ culture in Wilkins E medium such that the dermis of the skin was immersed in the medium but the epidermis was air facing.

Treatment of Skin with LGG Lysates 2.5, 5 or 7.5 µg of LGG lysates were applied to the stratum corneum of the organ cultured skin. A control culture was also prepared without LGG lysate. The skin cultures were incubated for 24 hours. The skin was then cryosectioned and immunostained for filaggrin expression using a commercially available antibody.

Statistical Analysis

All data was presented as the mean±SEM of three independent experiments with triplicate samples within each independent experiment.

Example 2

Figure 1:
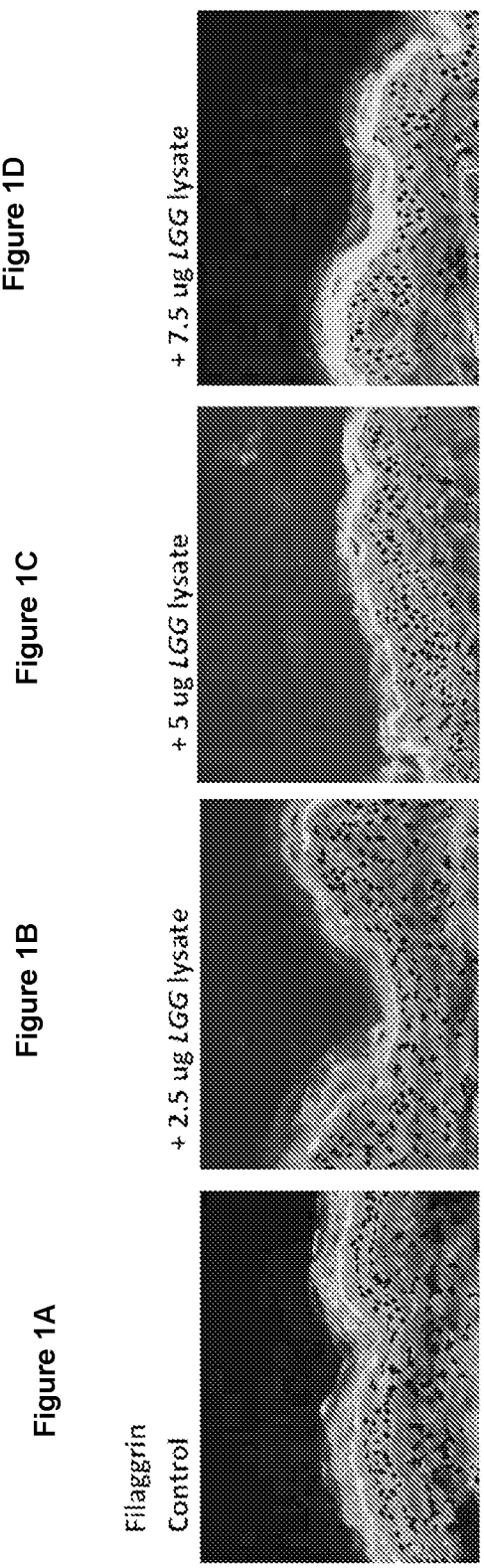
FIG. 1: Dose dependent effect of LGG lysate on filaggrin expression in normal human skin, where A: Control; B: 2.5 µg crude LGG lysate; C: 5 µg crude LGG lysate; and D: 7.5 µg crude LGG lysate.
Figure 2:
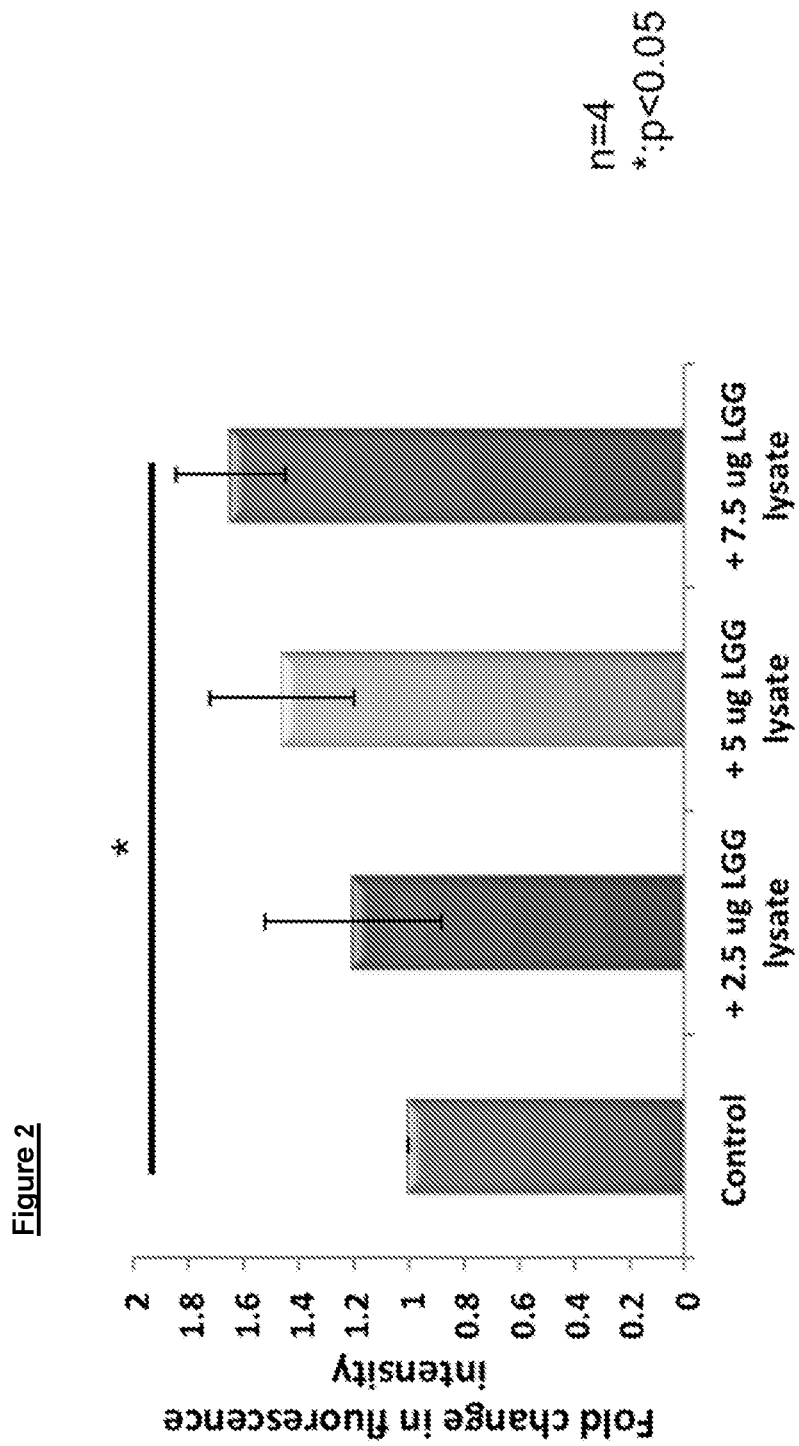
FIG. 2: Dose dependent effect of LGG lysate on filaggrin expression in normal human skin-change in fluorescence intensity

LGG Lysate Increases Filaggrin Expression in Normal Human Skin in a Dose Dependent Manner FIGS. 1A-D demonstrate that the signal for filaggrin, indicated in green, increases in a dose dependent manner when the sin is treated with increasing doses of LGG lysate. FIG. 2 also shows that filaggrin expression increased with an increasing amount of LGG lysate. The fold change in fluorescence intensity (of the stained filaggrin) increased as the amount of LGG lysate increased from nothing (control) to 7.5 µg.

The results show that LGG lysates can increase the expression of filaggrin in normal human skin.

The forgoing embodiments are not intended to limit the scope of the protection afforded by the claims, but rather to describe examples of how the invention may be put into practice.

REFERENCES

Mohammedsaeed M., et. al., (2014). *Appl. Environ. Microbiol.* 80(18):5773

Prince T. et. al., (2011) *Appl Environ. Microbiol.* 78(15):5119-26)

The invention claimed is:

1. A method of treating a skin or mucosa barrier dysfunction or defect associated with lowered and/or disrupted filaggrin or profilaggrin expression comprising topically administering a composition comprising a bioactive extract of *Lactobacillus rhamnosus* GG (LGG) (ATCC 53103), wherein from 8.8 µg/cm$^2$ to 26.5 µg/cm$^2$ of the bioactive extract of *Lactobacillus rhamnosus* GG (LGG) (ATCC 53103) is administered or applied to, or on, the skin or mucosa barrier surface.

2. The method according to claim 1, wherein the LGG and/or a bioactive extract of LGG is in lysate form.

3. The method according to claim 1, wherein the method increases and/or repairs skin barrier function.

4. The method according to claim 1, wherein the skin barrier dysfunction comprises atopic dermatitis.

5. The method according to claim 1, wherein the composition further comprises one or more pharmaceutically acceptable ingredients or excipients.

6. The method according to claim 1, which is formulated in the form of a cream, gel, ointment or oil.

* * * * *